US00PP12206P2

(12) United States Plant Patent
Colfer

(10) Patent No.: US PP12,206 P2
(45) Date of Patent: Nov. 20, 2001

(54) ARTICHOKE PLANT NAMED 'PS-IG0130'

(75) Inventor: William J. Colfer, Aptos, CA (US)

(73) Assignee: Seed Research Services, LLC, Salinas, CA (US)

( * ) Notice: Subject to any disclaimer, the term of this patent is extended or adjusted under 35 U.S.C. 154(b) by 0 days.

(21) Appl. No.: 09/482,569

(22) Filed: Jan. 14, 2000

(51) Int. Cl.[7] ..... A01H 5/00
(52) U.S. Cl. ..... Plt./258
(58) Field of Search ..... Plt./258

(56) References Cited

U.S. PATENT DOCUMENTS

P.P. 2,738 * 5/1967 Montgomery et al. ..... Plt./258

* cited by examiner

*Primary Examiner*—Bruce R. Campell
*Assistant Examiner*—Wendy C Baker
(74) *Attorney, Agent, or Firm*—Foley & Lardner

(57) ABSTRACT

A new and distinct cultivar of Artichoke plant named 'PS-IG0130' characterized by having large, non-glossy heads and thick, fleshy bracts and hearts. 'PS-IG0130' shows uniformity of head shapes and a reduced plant height.

3 Drawing Sheets

BACKGROUND OF THE INVENTION

The present invention comprises a new and distinct cultivar of artichoke plant, botanically known as *Cynara scolymus L.* and herein referred to by the cultivar name 'PS-IG0130'.

*Cynara scolymus L.,* commonly known as globe artichoke, is a thistle-like perennial herb and is a member of the family Asteraceae. Globe artichokes comprise leaves which are pinnately lobed but primarily spineless, globose capitula composed of overlapping layers of large involucral bracts, and receptacles which are enlarged and fleshy. Globe artichoke plants may be propagated by division and are essentially grown for the production of the immature flower heads, which are considered as vegetable delicacies. Fresh artichokes may be steamed or boiled, after which the fleshy receptacle, inner and outer bracts, and parts of the floral stem may be eaten.

The new cultivar is a product of a planned breeding program carried out by the inventor, William J. Colfer at Chowchilla, Calif. in 1996. 'PS-IG0130' was discovered and selected within the progeny of open-pollinated proprietary cultivar designated GGC3 by the inventor, William J. Colfer.

Asexual reproduction of the new cultivar by division was performed by the inventor in Watsonville, Calif. in 1997, and has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'PS-IG0130' which in combination distinguish this Artichoke as a new and distinct cultivar:

1. Large, non-glossy heads;
2. Thick, fleshy bracts and hearts;
3. Uniformity of head shapes; and
4. Reduced plant height.

'PS-IG0130' has not been observed under all possible environmental conditions. The phenotype of the new cultivar may vary with variations in environment such as temperature, humidity, light intensity and daylength, without any change in the genotype. The following observations, measurements and values describe the new cultivar as grown in Chowchilla, Calif. under conditions which closely approximate those generally used in horticultural practice.

Chowchilla is located in California's central San Juaquin valley. Conditions can vary greatly during the summer months. Air temperatures can range between the low 60's (F.) to temperatures well over 100° F. Relative humidity is generally low with values ranging from the mid 40's to the high 60's. Prevailing winds are westerly and rainfall averages rarely exceed 15" (inches) of rainfall.

In the following description, holding quality was measured by the physical appearance of the head. This includes the head's appearance following 3, 7 and 10-day storage periods in cold storage at 34° F. The head's exterior (oxidation) was observed at each of the three observation points. Browning and blackening of plant tissue was evaluated as light, moderate and extreme. Juiciness was measured by observing visible exudate and rated as absent, moderate-presence or excess. Overall storage response was measured by observing heads following 3, 7 and 10-day cold storage periods. These observations concentrated on visible color variability and/or presence of lesions or other cosmetic anomalies. Leaf ratio (L/W) was determined by dividing representative leaf sample lengths by their width. Finally, head response (weather) was determined by observing the heads at maturity. These field observations focus on the presence or absence of bronzing, necrotic or chlorotic lesions or any abiotic responses to environmental conditions.

BRIEF DESCRIPTION OF THE DRAWINGS

The accompanying color photographic illustrations show typical fruit and foliage characteristics of a specimen plant of 'PS-IG0130', with colors being as true as possible with illustrations of this type.

The first drawing is a side elevational view of the fruit and foliage.

The second drawing is a close-up view of the fruit showing its physical dimensions.

The third drawing is close-up view showing a vertical cross-section of the fruit.

DETAILED BOTANICAL DESCRIPTION

The following observations, measurements, and values describe the new cultivar as grown in Chowchilla, Calif. The data was collected from first year tissue culture outplants. Selections were made in outdoor field settings. Plants are grown in the soil in rows. Row spacing (bed centers) is 38 inches, individual plant spacing varies between 12–36 inches, depending upon original seed germination. Stem segments were used to develop shoots which were transferred to a rooting medium for root development. These plants were then transplanted into the greenhouse for final plant growth and development. The date of first harvest is approximately May 25 and the date of final harvest is approximately June 20.

Color references are measured against The Munsell Book of Color, Munsell Color Macbeth Division of Kollmorgen Corporation.

Parentage: 'PS-IG0130' was discovered and selected within the progeny of open-pollinated proprietary cultivar GGC3.

Classification: *Cynara scolymus L.* c.v. 'PS-IG0130'.

Propagation: Asexual production either by tissue culture using stem segments to develop shoots for root development or division.

Plant:

*Height.*—Approximately 36.83–81.28 cm.

*Width.*—Approximately 83.82–198.76 cm.

*Form.*—Intermediate full.

*Growth habit.*—Upright/intermediate.

*Plant vigor.*—7.62 cm (2–3 leaves)–81.28 cm (18–58 leaves) from fall planting (mid October) to final harvest (following May).

*Side shoots.*—Number: Approximately 2–4. Development: Poor. Length: 20.2–93.5 cm, average 62.57 cm. Diameter: 16.0 mm–22.0 mm, average 18.8 mm. Color: Pubescence with color range: 5GY 9/2–2.5GY 9/2–2.5GY 9/4; anthocyanin present on the basal portion of the shoot, color range: 7.5R 6/4–7.5R 5/4–7.5R 4/4.

*Main stem.*—Length: 20.5–30.0 cm, average 23.75 cm. Diameter: 32.0–41.0 mm, average 36.20 mm. Color: Light pubescence, color range: 5GY 9/2–2.5GY 9/2–2.5GY 9/4. Leaves on Main Stem: Approximately 10–16, average 13 leaves.

*Foliage density.*—Open; side-shoot development is reduced; low foliage density.

Capitulum:

*Size.*—Primary: Approximately 33.66–38.10 cm. Secondary: Approximately 18.42–27.94 cm.

*Shape.*—Oval to oval-spherical.

*Number.*—Approximately 1–3 per plant.

*Texture.*—Intermediate, smooth.

*Fragrance.*—Mild.

*Bract size.*—Length: Approximately 8.2–9.6 cm. Width: Approximately 5.2–5.6 cm.

*Bract shape.*—Predominantly oval-shaped.

*Bract texture.*—Smooth, slight texture.

*Bract number.*—Approximately 58–64 per head.

*Bract color.*—Inner: 10 Y 9/1–10 Y 9/2. Outer: 2.5 GY 9/2–2.5 GY 9/4.

*Bract firmness.*—Firm, thick, fleshy and well attached.

*Bract basal thickness.*—Approximately 6.0–9.0 mm.

*Heart description.*—Concave and full with a slightly reduced shoulder.

*Heart color.*—10 Y 9/1–10 Y 9/2.

*Pappus length.*—Approximately 2.2–2.7 cm.

*Pappus color.*—Variable white coloration, range: 10Y 9/2–10Y 9/4.

*Overall cold storage response.*—Good, no browning or blackening of any capitula tissue was observed.

*Head firmness.*—Firm, heads (capitula) are dense and hard.

*Gloss.*—Dull, no sheen or glossiness visible.

*Cold storage (hold quality).*—Good, heads remain firm and free of decay.

*Head exterior (oxidation).*—Light; some tissue is slightly browned.

*Juiciness.*—Moderate presence, some exudate presence following stem cuts.

*Head response (weather).*—No adverse responses to weather conditions were observed on heads (capitula) or other plant tissues.

*Bud burst.*—April 20–April 25.

*Bloom time.*—Approximately May 25–June 10.

*Duration of bloom.*—Approximately 35–40 days.

*Bloom diameter.*—7.49–13.34 cm; average 10.87 cm.

*Bloom depth.*—9.53–10.8 cm; average 10.20 cm.

*Bloom shape.*—Head.

*Florets.*—978–1178 florets per head, average 1083 florets per head.

*Bud weight.*—Primary bud weight 446.3–489.25 grams, average 472.37 grams; secondary bud weight 330.6–347.6 grams, average 342.70 grams.

Foliage:

*Length.*—Approximately 74.2–99.7 cm.

*Width.*—Approximately 41.2–56.2 cm.

*Leaf serrations.*—Approximately 4.7–12.6 cm.

*Leaf basal angle.*—Approximately 25–50 degrees.

*Leaf ratio (L/W).*—Approximately 1.43–1.91.

*Leaf area.*—Approximately 2890.7–5586.2 $cm^2$.

*Upper leaf surface color.*—Highly pubescent, color range: 5GY 8/2–5GY 7/2–5GY 7/4.

*Lower leaf surface color.*—Highly pubescent, color range: 5GY 7/4–5 GY 7/6–5GY 6/6.

*Texture.*—Slightly textured; leaves have raised bump epidermis which is not blister-like.

*Venation.*—Intermediate green; mid-vein is white to pale green, 2.5 GY 7/6 to 2.5 GY 6/6; lobes are green and indistinct.

*Pubescence.*—Moderate density; younger leaves have dense pubescence; older leaves are smooth and free of pubescence.

*Leaf basal thickness.*—Approximately 9.0–18.0 mm.

*Leaf distance between serrations.*—Approximately 2.0–5.6 cm.

*Petiole length.*—Approximately 4.0–14.6 cm.

*Petiole width.*—Approximately 2.5–4.2 cm.

*Petiole color.*—Color range: 5GY 7/4–5GY 7/6–5GY 6/6, slight anthocyanin coloration on basal portion, color range: 7.5R 6/4–7.5R 5/4–7.5R 4/4.

Seeds:

*Shape.*—Compressed ovoid, can be angular, asymmetrical mid-section.

*Number.*—12–108 seeds per head; average 51.0 seeds per head.

*Length.*—7.0–8.0 mm; average 7.22 mm.

*Width.*—3.0–5.0 mm; average 4.33 mm.

*Color.*—Light brown, some tan hues, speckled pattern.

Plant/bud disease resistance/susceptibility: Moderate infection of powdery mildew, *Leveillula taurica,* Ramularia spp. and Alternaria spp. leaf spot were noted; infection was observed in the plant's lower canopy.

General observations: 'PS-IG0130' plants exhibit moderate height ranging from 36–81 cm. The head quality of 'PS-IG0130' compared to artichoke variety Green Globe are thicker fleshy bracts, thicker fleshy hearts (receptacles), oval shape and green (non-glossy) exterior coloration. The non-glossy heads (capitula) are large. 'PS-IG0130' produces an average size (12) primary, size (18) secondary and an occasional tertiary, size (36). Head numbers are reduced in this cultivar ranging between 1–3 heads per plant. Anthocyanin coloration is visible on both interior bracts and exterior lower bracts. The head spinosity is reduced with average spine length of approximately 1–2 mm. Some bracts actually display intermediate notching. The plants upright growth is intermediate, compact and displays moderate vigor. The canopies' coloration is a medium green/yellow color ranging from medium to darker shades. These colors range on the Munsell Leaf Color Chart 5 GY 4/6–5 GY 3/4–5 GY 4/4. Canopy coloration can vary from plant to plant and leaf to leaf, due to the leaf's overall sun exposure in relation to another leaf on the same plant. The rosette plant development clusters leaves that can shade lower leaf structures of the same age, effecting leaf coloration. Leaf spinosity is moderate, categorized as few. Floral stalk development during anthesis produces a purple flower, color range: 10P 5/10–10P 5/12–10P4/12–10P 4/10.

I claim:

1. A new and distinct cultivar of Artichoke plant named 'PS-IG0130', as described and illustrated.

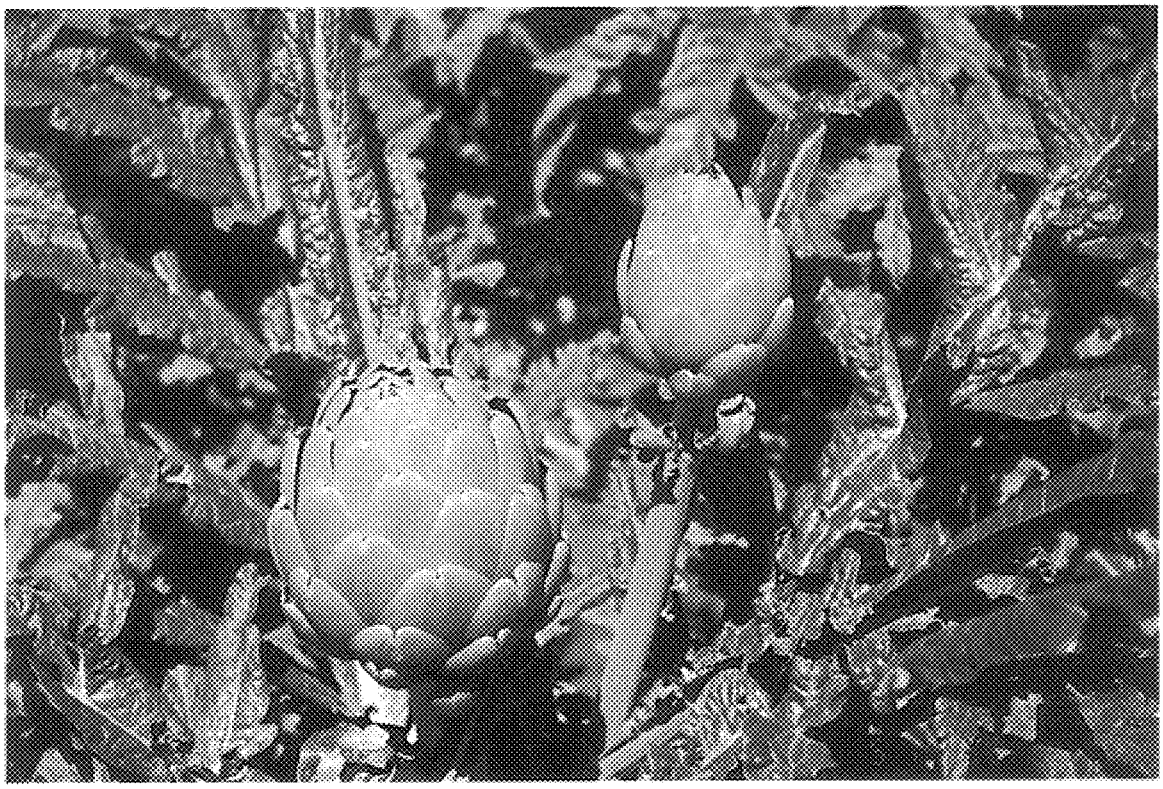

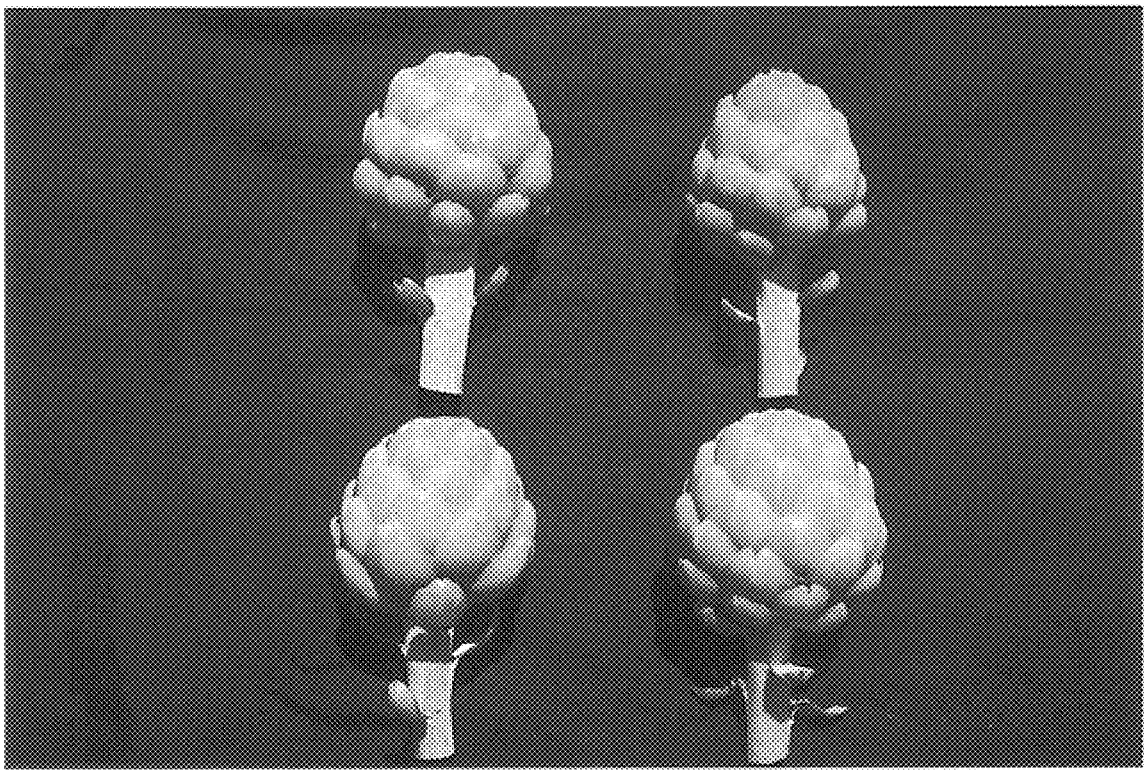

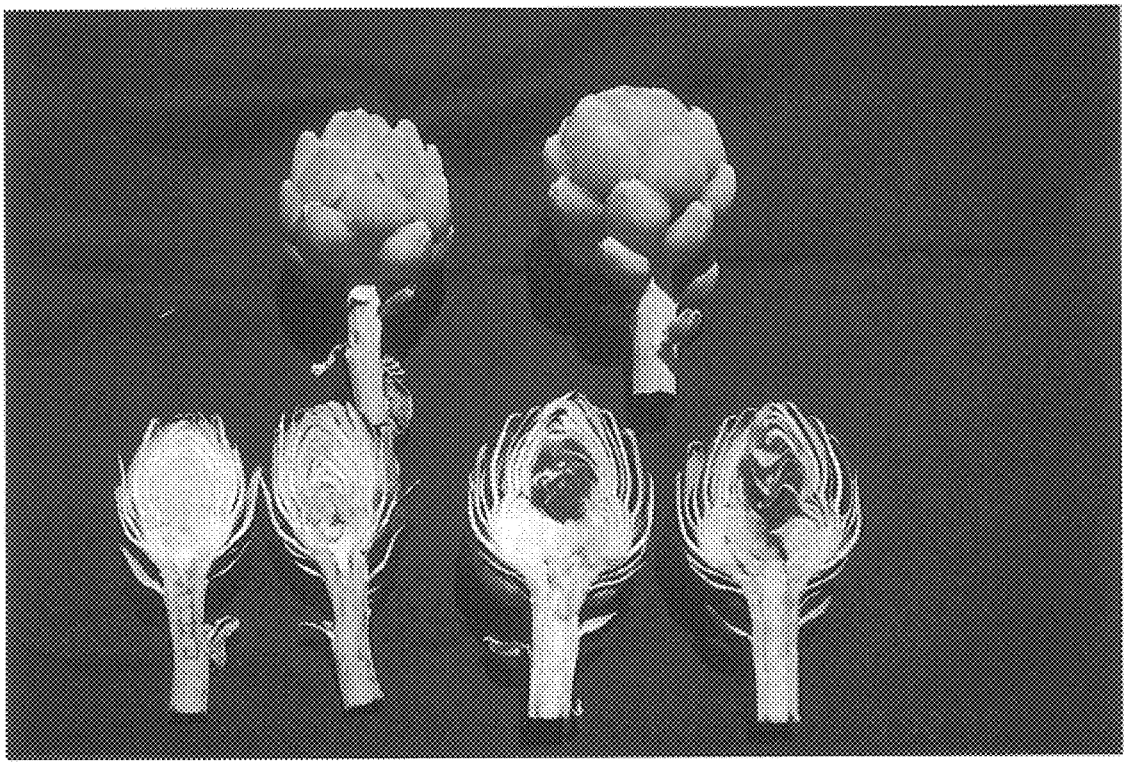

* * * * *